United States Patent [19]

Carson et al.

[11] Patent Number: 4,663,332
[45] Date of Patent: May 5, 1987

[54] 5-SUBSTITUTED N-ALKYLATED TETRAZOLES

[75] Inventors: Matthew Carson, Nutley; Ronald A. LeMahieu, North Caldwell, both of N.J.

[73] Assignee: Hoffman-La Roche Inc., Nutley, N.J.

[21] Appl. No.: 786,386

[22] Filed: Oct. 10, 1985

[51] Int. Cl.$^4$ .................... C07D 401/06; A61K 31/44
[52] U.S. Cl. .................................... 514/340; 546/276; 548/252; 514/381
[58] Field of Search ........................ 546/276; 514/340

[56] References Cited

U.S. PATENT DOCUMENTS 4,105,852  8/1978  Hassall et al. ........................ 546/276

FOREIGN PATENT DOCUMENTS 0108592  5/1984  European Pat. Off. .
0110541  6/1984  European Pat. Off. .

OTHER PUBLICATIONS

The Journal of Pharmacology and Experimental Therapeutics, vol. 233, No. 1 (1985).
Naunyn–Schmiedeverg's Avch. Pharmacol. (1986) 333; 70–77.

Primary Examiner—Jane T. Fan
Attorney, Agent, or Firm—Jon S. Saxe; Bernard S. Leon; Matthew Boxer

[57] ABSTRACT

Compounds of the formula

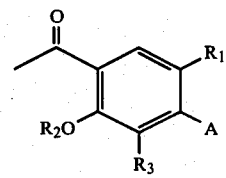

I wherein $R_1$, $R_2$, $R_3$, and A are as described herein, are set forth.

These compounds are useful as anti-allergic agents and agents for the treatment of cardiovascular diseases.

23 Claims, No Drawings

5-SUBSTITUTED N-ALKYLATED TETRAZOLES

BRIEF SUMMARY OF THE INVENTION

The invention relates to compounds of the formula

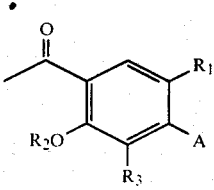

I wherein $R_1$ is hydrogen or halogen; $R_2$ is hydrogen or $C_2$-$C_4$ alkanoyl; $R_3$ is hydrogen or $C_1$-$C_6$ alkyl; A is —O—(CH$_2$)$_n$—B or,

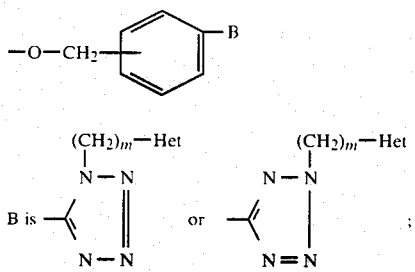

Het is a 5- or 6-membered heterocycle, containing one or two nitrogens and optionally mono-substituted by $C_1$-$C_6$ alkyl; n is an integer from 3 to 8; and m is an integer from 1 to 6; or pharmaceutically acceptable acid addition salts thereof. The compounds of formula I are useful as anti-allergic agents and agents for the treatment of cardiovascular diseases.

DETAILED DESCRIPTION OF THE INVENTION

As used herein, the term "alkyl" denotes straight or branched chain alkyl of up to 12 carbon atoms, or the number of carbon atoms otherwise designated. Thus $C_1$-$C_6$ alkyl denotes a straight or branched chain alkyl of up to six carbon atoms. The term "alkyl" includes, for example, methyl, ethyl, propyl, isopropyl, butyl, t-butyl and the like. The term "alkanoyl" denotes a straight or branched chain alkanoyl of one to six carbon atoms, or the number of carbon atoms otherwise designated. The term "alkanoyl" includes, for example, acetyl, propionyl, iso-butyryl and the like. As used herein the term "halogen" denotes chlorine, bromine, iodine and fluorine.

The invention relates to compounds of the formula

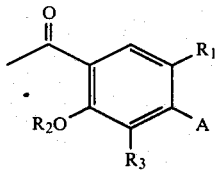

I wherein $R_1$ is hydrogen or halogen; $R_2$ is hydrogen or $C_2$-$C_4$ alkanoyl;

$R_3$ is hydrogen or $C_1$-$C_6$ alkyl; A is —O(CH$_2$)$_n$—B, or

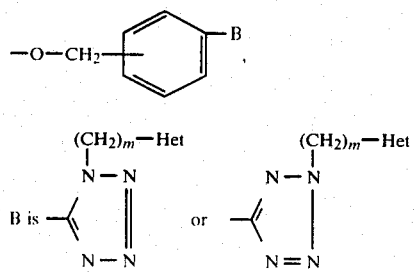

Het is a 5- or 6-membered heterocycle, containing one or two nitrogens and optionally monosubstituted by $C_1$-$C_6$ alkyl, preferably 3-pyridyl, 4-pyridyl or 1-imidazolyl;

n is an integer from 3 to 8; and m is an integer from 1 to 6; or a pharmaceutically acceptable acid addition salt thereof.

Preferred compounds of formula I are those wherein $R_1$ is chlorine; $R_2$ is hydrogen; $R_3$ is propyl; A is —O—(CH$_2$)$_n$—B;
B is

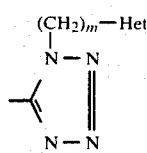

Het is 3-pyridyl, n is an integer from 3 to 5 and m is an integer from 1 to 4.

Other preferred compounds of formula I are those wherein $R_1$ is hydrogen; $R_2$ is hydrogen; $R_3$ is propyl; A is —O—(CH$_2$)$_n$—B;
B is

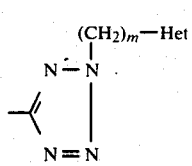

Het is 3-pyridyl, n is an integer from 3 to 5, and m is an integer from 1 to 4, or preferably from 3 to 4.

Still other preferred compounds of formula I are those wherein $R_1$ is hydrogen; $R_2$ is hydrogen; $R_3$ is propyl; A is —O—(CH$_2$)$_n$—B;
B is

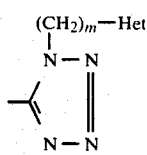

Het is 3-pyridyl, n is an integer from 3 to 5; and m is an integer from 1 to 4, preferably from 3 to 4.

Exemplary compounds of formula I are:
1-[2-hydroxy-3-propyl-4-[4-[1-[3-(1H-imidazol-1-yl)propyl]-1H-tetrazol-5-yl]butoxyl]phenyl]ethanone;

1-[2-hydroxy-3-propyl-4-[4-[2-[3-(1H-imidazol-1-yl)propyl-2H-tetrazol-5-yl]butoxyl]phenyl]ethanone;
1-[2-hydroxy-3-propyl-4-[[3-[1-[3-(3-pyridinyl)propyl]-1H-tetrazol-5-yl]phenyl]methoxy]phenyl]ethanone;
1-[2-hydroxy-3-propyl-4-[[3-[2-[3-(3-pyridinyl)propyl]-2H-tetrazol-5-yl]phenyl]methoxy]phenyl]ethanone;
1-[2-hydroxy-3-propyl-4-[[3-[2-(1H-imidazol-1-yl)propyl]-2H-tetrazol-5-yl]phenyl]methoxy]phenyl]ethanone;
1-[5-chloro-2-hydroxy-3-propyl-4-[5-[1-[4-(3-pyridinyl)butyl]-1H-tetrazol-5-yl]pentyloxy]phenyl]ethanone;
1-[2-acetoxy-3-propyl-4-[5-[1-[3-(3-pyridinyl)propyl]-1H-tetrazol-5-yl]pentyloxy]phenyl]ethanone;
1-[2-hydroxy-3-propyl-4-[5-[2-[3-(3-pyridinyl)propyl]-2H-tetrazol-5-yl]pentyloxy]phenyl]ethanone;
1-[2-hydroxy-3-propyl-4-[3-[2-[3-(3-pyridinyl)propyl]-2H-tetrazol-5-yl]propoxy]phenyl]etanone;
1-[2-hydroxy-3-propyl-4-[4-[2-[3-(3-pyridinyl)propyl]-2H-tetrazol-5-yl]butoxy]phenyl]ethanone;
1-[2-hydroxy-3-propyl-4-[5-[1-[4-(3-pyridinyl)butyl]-1H-tetrazol-5-yl]pentyloxy]phenyl]ethanone;
1-[2-hydroxy-3-propyl-4-[3-[1-[4-(3-pyridinyl)butyl]-1H-tetrazol-5-yl]propoxy]phenyl]ethanone;
1-[2-hydroxy-3-propyl-4-[3-[2-[4-(3-pyridinyl)butyl]-2H-tetrazol-5-yl]propoxy]phenyl]ethanone;
1-[2-hydroxy-3-propyl-4-[5-[2-(3-pyridinyl)methyl]-2H-tetrazol-5-yl]pentyloxy]phenyl]ethanone;
1-[2-hydroxy-3-propyl-4-[4-[1-[2-(3-pyridinyl)ethyl]-1H-tetrazol-5-yl]butoxy]phenyl]ethanone;
1-[2-hydroxy-3-propyl-4-[4-[2-[2-(3-pyridinyl)ethyl]-2H-terazol-5-yl]butoxy]phenyl]ethanone;
1-[2-hydroxy-3-propyl-4-[4-[1-[3-(3-pyridinyl)propyl]-1H-tetrazol-5-yl]butoxy]phenyl]ethanone; and
1-[-hydroxy-3-propyl-4-[4-[2-[3-(3-pyridinyl)propyl-2H-tetrazol-5-yl]butoxy]phenyl]ethanone.
1-[2-hydroxy-3-propyl-4-[5-[1-[2-(3-pyridinyl)ethyl]-1H-tetrazol-5-yl]pentyloxy]phenyl]ethanone;
1-[2-hydroxy-3-propyl-4-[4-[1-[1-(3-pyridinyl)methyl]-1H-tetrazol-5-yl]butoxy]phenyl]ethanone;
1-[2-hydroxy-3-propyl-4-[4-[1-[4-(3-pyridinyl)butyl]-1H-tetrazol-5-yl]butoxy]phenyl]ethanone;
1-[2-hydroxy-3-propyl-4-[3-[1-[2-(3-pyridinyl)ethyl]-1H-tetrazol-5-yl]propoxy]phenyl]ethanone;
1-[2-hydroxy-3-propyl-4-[3-[1-[1-(3-pyridinyl)methyl]-1H-tetrazol-5-yl]propoxy]phenyl]ethanone;
1-[2-hydroxy-3-propyl-4-[3-[1-[5-(3-pyridinyl)pentyl]-1H-tetrazol-5-yl]propoxy]phenyl]ethanone;
1-[2-hydroxy-3-propyl-4-[5-[2-[2-(3-pyridinyl)ethyl]-2H-tetrazol-5-yl]pentyloxy]phenyl]ethanone;
1-[2-hydroxy-3-propyl-4-[4-[2-[1-(3-pyridinyl)methyl]-2H-tetrazol-5-yl]butoxy]phenyl]ethanone;
1-[2-hydroxy-3-propyl-4-[4-[2-[4-(3-pyridinyl)butyl]-2H-tetrazol-5-yl]butoxy]phenyl]ethanone;
1-[2-hydroxy-3-propyl-4-[5-[1-[3-(1H-imidazol-1-yl)propyl]-1H-tetrazol-5-yl]pentoxy]phenyl]ethanone;
1-[2-hydroxy-3-propyl-4-[5-[2-[3-(1H-imidazol-1-yl)propyl]-2H-tetrazol-5-yl]pentoxy]phenyl]ethanone;
1-[2-hydroxy-3-propyl-4-[[2-[2-(1H-imidazol-1-yl)ethyl]-2H-tetrazol-5-yl]phenyl]methoxy]phenyl]ethanone;
1-[2-hydroxy-3-propyl-4-[[4-[2-(1H-imidazol-1-yl)butyl]-2H-tetrazol-5-yl]phenyl]methoxy]phenyl]ethanone;
1-[2-hydroxy-3-propyl-4-[[3-[1-[2-(3-pyridinyl)ethyl]-1H-tetrazol-5-yl]phenyl]methoxy]phenyl]ethanone;
1-[2-hydroxy-3-propyl-4-[[3-[1-[4-(3-pyridinyl)butyl]-1H-tetrazol-5-yl]phenyl]methoxy]phenyl]ethanone;
1-[2-hydroxy-3-propyl-4-[[3-[2-[2-(3-pyridinyl)ethyl]-2H-tetrazol-5-yl]phenyl]methoxy]phenyl]ethanone;
1-[2-hydroxy-3-propyl-4-[[3-[2-[4-(3-pyridinyl)butyl]-2H-tetrazol-5-yl]phenyl]methoxy]phenyl]ethanone;
1-[5-chloro-2-hydroxy-3-propyl-4-[[3-[1-[3-(3-pyridinyl)propyl]-1H-tetrazol-5-yl]phenyl]methoxy]phenyl]ethanone;
1-[2-hydroxy-3-propyl-4-[5-[2-[4-(3-pyridinyl)butyl]-2H-tetrazol-5-yl]pentyloxy]phenyl]ethanone;
1-[2-hydroxy-3-propyl-4-[5-[1-[4-(3-pyridinyl)butyl]-1H-tetrazol-5-yl]pentyloxy]phenyl]ethanone;
1-[2-hydroxy-3-propyl-4-[3-[1-[3-(3-pyridinyl)propyl]-1H-tetrazol-5-yl]propoxy]phenyl]ethanone; and
1-[2-hydroxy-3-propyl-4-[5-[1-(3-pyridinyl)methyl]-1H-tetrazol-5-yl]pentyloxy]phenyl]ethanone.

Most preferred compounds of formula I are;
1-[2-hydroxy-3-propyl-4-[5-[1-[3-(3-pyridinyl)propyl]-1H-tetrazol-5-yl]pentyloxy]phenyl]ethanone; and
1-[2-hydroxy-3-propyl-4-[4-[1-[3-(3-pyridinyl)propyl]-1H-tetrazol-5-yl]butoxy]phenyl]ethanone.

The preparation of the compounds of formula I is exemplified as hereinafter described.

A compound of the formula

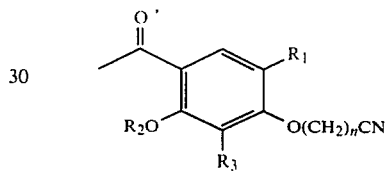

wherein $R_1$, $R_2$, $R_3$ and n are as previously described, is reacted with sodium azide and ammonium chloride to yield a tetrazole of the formula

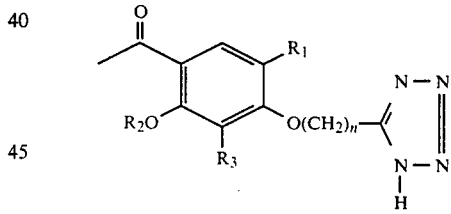

wherein $R_1$, $R_2$, $R_3$, and n are as previously described. Compounds of formula II are known compounds or can be prepared according to known methods.

The reaction is run with an excess of sodium azide, in a polar, aprotic solvent such as anhydrous dimethylacetamide, or, more preferably, anhydrous dimethylformamide, at a temperature in a range from about 80° to about 120°. The product is recovered by usual means, such as crystallization.

A compound of formula III is converted to the N-1 and N-2 isomers of formulas Ia and Ib respectively

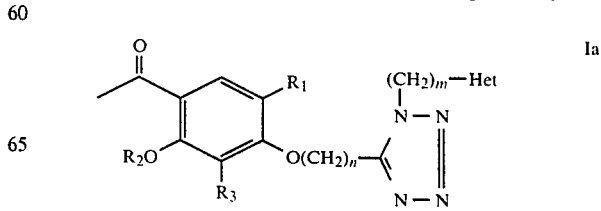

and

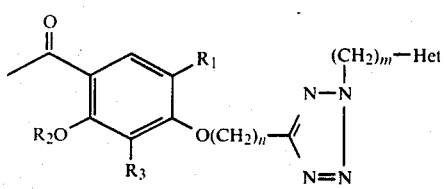

wherein $R_1$, $R_2$, $R_3$, n, m, and Het are as previously described, by reaction with a compound of formula

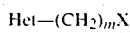    IV wherein m, X and Het are as previously described. Compounds of formula IV are known compounds or can be prepared according to known methods. The reaction is carried out in a polar, aprotic solvent such as anhydrous methyl ethyl ketone, anhydrous acetone, anhydrous dimethylformamide, or most preferably a mixture of anhydrous acetone and anhydrous dimethylformamide. The reaction is conducted at elevated temperatures, up to the reflux temperature of the particular solvent system used. When anhydrous dimethylformamide is used the reaction is conducted at a temperature from about 50° to about 120°. The reaction is conducted in the presence of a base such as an alkali metal carbonate, like lithium carbonate, sodium carbonate, or more preferably potassium carbonate; a lower alkyl tertiary amine such as tripropylamine, tributylamine, or more preferably triethylamine or tributylstannyloxide. Separation of compounds of formula Ia and Ib can be carried out by known chromatographic techniques such as column chromatography or high pressure liquid chromatography.

A compound of Ia or Ib, wherein $R_2$ is hydrogen can be converted to a corresponding compound of Ia or Ib wherein $R_2$ is alkanoyl, by reaction with an alkanoyl anhydride, at elevated temperature, in the presence of an organic base. For example, compounds of formula Ia or Ib wherein $R_2$ is acetyl can be prepared by reacting a compound of formula Ia or Ib with acetic anhydride, in pyridine, at a temperature of from about 50° to about 100°.

Compounds of formula Ia and Ib are encompassed by compounds of formula I.

The compounds of formula Ia can also be prepared by reacting an amide of the formula

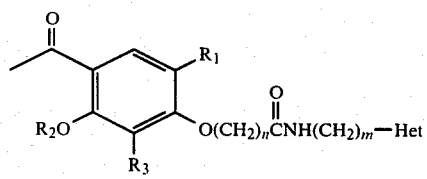

wherein $R_1$, $R_2$, $R_3$, n, m, and Het are as previously described, first with phosphorous pentachloride and then with an excess of hydrazoic acid to obtain,

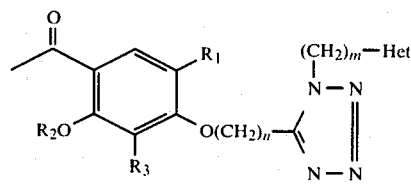

wherein $R_1$, $R_2$, $R_3$, n, m and Het are as previously described.

The reaction is carried out in an anhydrous halo alkane solvent such as anhydrous chloroform. There is added an excess of hydrazoic acid. The temperature of the reaction is from about 0° to about 30° during addition of the phosphorous pentachloride and from 30° up to the reflux temperature of the solvent system used afterwards.

The amide of formula V can be obtained as follows: an acid of the formula

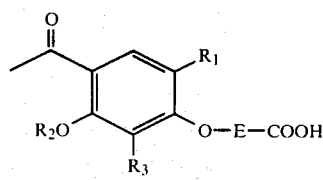

wherein $R_1$, $R_2$, and $R_3$ are as described above and E is —$(CH_2)_n$— can be converted to an amide of the formula

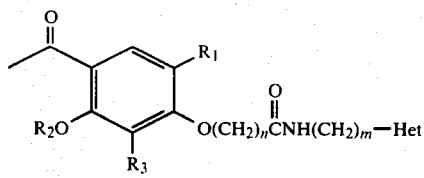

wherein $R_1$, $R_2$, $R_3$, n, m and Het are as described above.

The conversion of an acid of formula VIa to the desired intermediate of formula V is carried out as follows. A compound of formula VIa is converted to an intermediate acid azide by reaction with diphenylphosphoryl azide in an anhydrous polar solvent, such as, dimethylformamide, at a temperature in the range of from about 0° to about 25° C., preferably at about 5° C., and in the presence of an organic base, such as, a trialkylamine, for example, triethylamine. The reaction mixture containing the acid azide is then treated with an amine of formula

    VII wherein m and Het are as described above, which are known compounds, at a temperature in the range of from about 0° to about 25° C., to give the corresponding intermediate of formula V which can be separated by known procedures, for example, crystallization, chromatography and the like.

Alternatively, a compound of formula

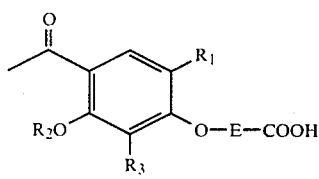

VIa wherein $R_1$, $R_2$, and $R_3$ are as described above and E is —$(CH_2)_n$— is converted to an intermediate imidazolide by treatment with 1,1'-carbonyldiimidazole in an anhydrous inert solvent, such as, tetrahydrofuran, at a temperature in the range of from about 0° to about 25° C., preferably at about 25° C. The obtained imidazolide is immediately allowed to react with an amine of formula VII at about 25° to give the corresponding intermediate of the formula.

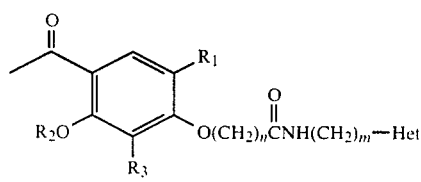

V wherein $R_1$, $R_2$, $R_3$, n, m and Het are as described above.

Compounds of formula Ic can be prepared by reacting an amide of the formula

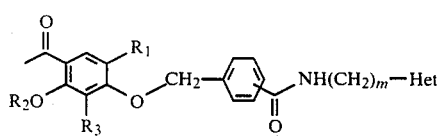

VIII wherein $R_1$, $R_2$, $R_3$, m, and Het are as previously described, with phosphorous pentachloride followed by an excess of hydrazoic acid to obtain

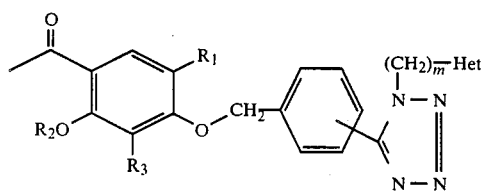

Ic wherein $R_2$, $R_3$, m and Het are as previously described, and $R_1$ is halogen. The reaction is carried out in an analogous manner to that described above for the conversion of a compound of formula V to a compound of formula Ia. Compounds of formula Ic are encompassed by compounds of formula I.

An amide of formula VIII can be obtained in a manner analogous to that described above for the preparation of an amide of V, by employing as a starting material an acid of the formula

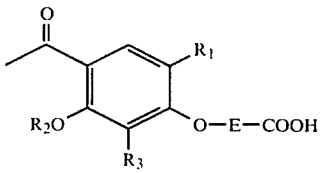

VIb wherein $R_2$ and $R_3$ is as previously described $R_1$ is hydrogen, and E is

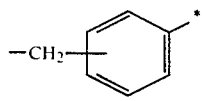

where * indicates the bond is attached to —COO.

Compounds of formula Ic and Id can be prepared by reacting an acetophenone of the formula

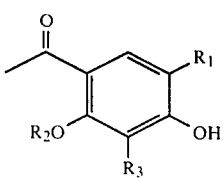

IX wherein $R_1$, $R_2$ and $R_3$ are as previously described, which are known compounds or can be prepared according to known methods, with a substituted nitrile of the formula

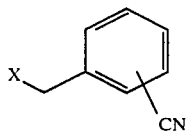

XI wherein X is as previously described, which are known compounds or can be prepared according to known methods, to obtain a compound of the formula

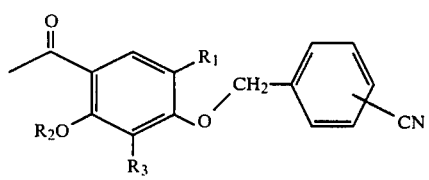

X wherein $R_1$, $R_2$ and $R_3$ are as previously described. The reaction is carried out in a ketone such as acetone or methylethyl ketone, or a polar aprotic solvent such as dimethylformamide or the like. The temperature of the reaction is from about 50° to 100°. The reaction is conducted in the presence of an inorganic base such as an alkali metal carbonate such as potassium carbonate, sodium carbonate or the like. Separation of a compound of formula X is by known techniques such as crystallization, chromatography or the like. Compounds of formula XI are known compounds or can be prepared according to known methods.

A compound of formula X is then reacted with an alkali metal azide such as preferably sodium azide, and ammonium chloride to obtain a compound of the formula

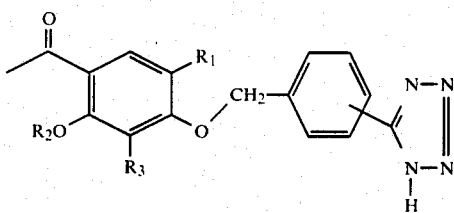   XII wherein $R_1$, $R_2$ and $R_3$ are as previously described.

The reaction is carried out in an analogous manner to that described above for the conversion of a compound of formula II to a compound of formula III.

A compound of formula XII is then reacted with a compound of formula

Het—$(CH_2)_m$X   IV wherein m, X and Het are as previously described to obtain a compound of the formula

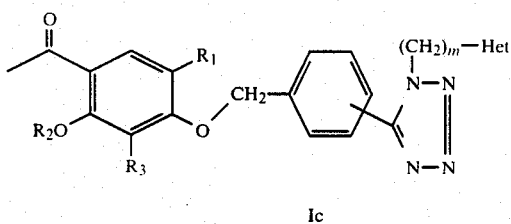

Ic

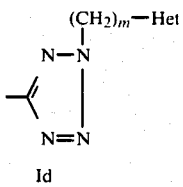

Id wherein $R_1$, $R_2$, $R_3$, m and Het are as previously described.

A compound of formula Ic or Id, wherein $R_2$ is hydrogen can be converted to a corresponding compound of formula Ic or Id wherein $R_2$ is alkanoyl by reaction with an alkanoyl anhydride, at elevated temperature, in the presence of an organic base. For example, compounds of formula Ic or Id wherein $R_2$ is

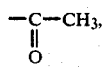

can be prepared by reacting a compound of formula Ic or Id wherein $R_2$ is hydrogen with acetic anhydride, in pyridine, at a temperature of from about 50° to about 100°. Compounds of formula Id are encompassed by compounds of formula I.

The intermediates of formulas VIa and VIb which are encompassed by the formula

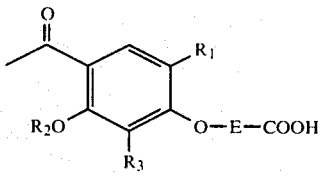   VI wherein $R_1$, $R_2$, and $R_3$ are as previously described, and E is

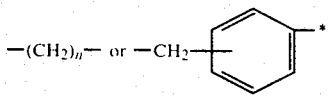

where * indicates the bond is attached to —COO— can be prepared as hereinafter described in Formula Scheme I.

Formula Scheme 1

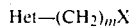

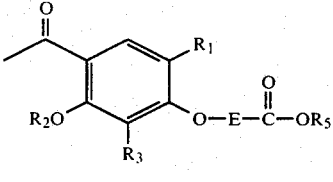

XIV

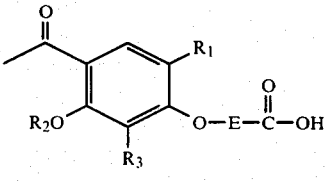

VI wherein $R_1$, $R_2$, $R_3$, E and X are as previously described and $R_5$ is $C_1$-$C_6$ alkyl.

In Formula Scheme I, a process for preparing the starting materials of formula VI is set forth. The reaction between a compound of formula IX and a compound of formula XIII, which are known compounds or can be prepared according to known procedures, is carried out in an inert solvent, for example, a ketone, preferably acetone or methyl ethyl ketone, or dimethyl formamide in the presence of a base, such as, an alkali metal carbonate, preferably potassium carbonate. The reaction is carried out at a temperature in the range of from about 25° to about 100°. The product of formula XIV is converted to the corresponding acid of formula VI by hydrolysis with an alkali metal hydroxide, such as, sodium hydroxide, in an aqueous alkanol, such as, methanol or ethanol, at a temperature in the range of from about 25° to about the boiling point of the reaction mixture. The obtained compound of formula VI can be separated by known procedures, for example, by crystallization, chromatography and the like.

The intermediates of formula VI can also be prepared as hereinafter described in Formula Scheme II.

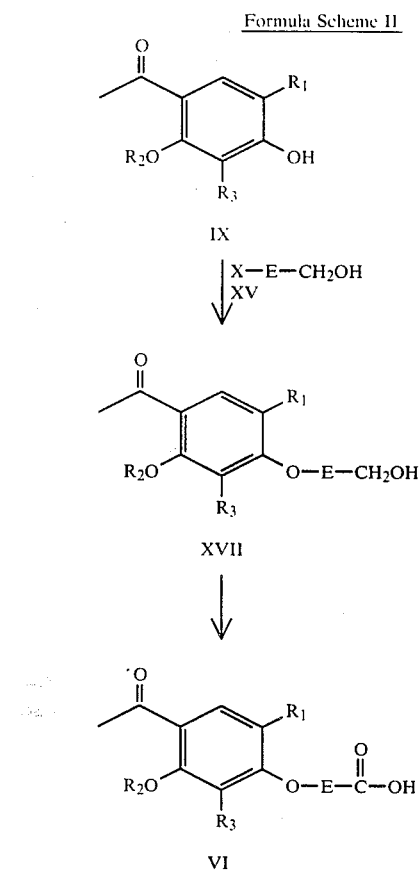

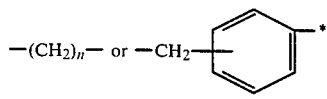

where * indicates the bond is attached to —CH$_2$O— or —COO—.

In Formula Scheme II, a compound of formula IX, which are known compounds or can be prepared according to known procedures, is alkylated with a halo alcohol of formula XV, which are known compounds or can be prepared according to known procedures, in a solvent, such as, acetone or dimethyl formamide in the presence of a base, such as, an alkali metal carbonate, preferably, potassium carbonate, at a temperature in the range of from about 50° to about 100° C. An alkali metal iodide may be used to facilitate the reaction. The product obtained of formula XVII is then oxidized under standard Jones oxidation conditions, which comprise treatment with chromium trioxide and sulfuric acid in an inert solvent, such as, acetone at a temperature of from about 0° to about 25° C., to yield the corresponding acid of formula VI. The obtained compound of formula VI can be separated by known procedures, for example, crystallization, chromatography and the like.

The intermediates of formula VI can also be prepared as hereinafter described in Formula Scheme III.

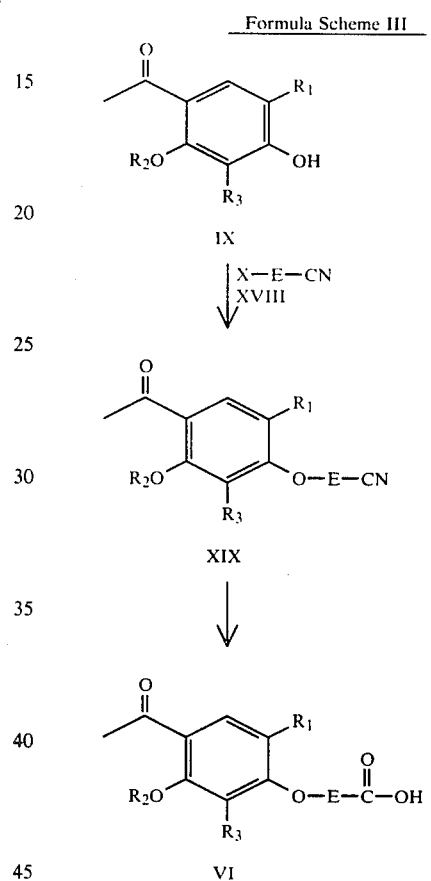

wherein R$_1$, R$_2$, R$_3$, and X are as previously described, and E is

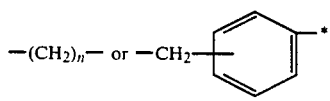

where * indicates the bond is attached to —CN or to —COO—.

In Formula Scheme III, a compound of formula IX, which are known compounds or can be prepared according to known procedures, is allowed to react with a halo nitrile of formula XVIII, which are known compounds or can be prepared according to known procedures, in a solvent, such as, acetone or dimethyl formamide in the presence of a base, such as, potassium carbonate at a temperature in the range of from about 50° to about 100° C. A nitrile of formula XIX may be converted to the corresponding starting acid VI by conventional means for converting a nitrile to an acid, for example, by treatment with sodium hydroxide in methanol over a steam bath, followed by acidification. A compound of formula VI can be separated by known procedures, for example, crystallization, chromatography and the like.

The compounds of formula I form addition salts with pharmaceutically acceptable organic or inorganic acids such as hydrochloric, hydrobromic, hydroiodic, other mineral acid salts such as sulfate, nitrate, phosphate and the like; alkyl- and mono-arylsulfonates such as ethanesulfonate, toluenesulfonate, benzenesulfonate, or the like; other organic acid salts such as acetate, tartrate, maleate, citrate, benzoate, salicylate, ascorbate and the like. Non-pharmaceutically acceptable acid addition salts of compounds of formula I above can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable anion.

The compounds of formula I, including the salts of pharmaceutically acceptable acids thereof possess anti-allergic activity and activity against cardiovascular diseases, whch renders them highly desirable as anti-allergic agents and agents in the treatment of cardiovascular diseases.

In addition, some of the compounds of formula I have shown oral activity at 100 mg/kg, against arrhythmias and hypertension.

The compounds of formula I of the invention are antagonists of platelet activating factor (PAF) and inhibitors of thromboxane $A_2$ synthesis ($TXA_2$). Accordingly, the compounds of formula I are useful in the treatment of allergic conditions such as allergic asthma as well as various cardiovascular diseases involving platelet aggregation such as unstable angina.

The useful anti-allergic activity and activity in treating cardiovascular diseases of the compounds of formula I and their salts is demonstrated in vitro and in warm-blooded animals utilizing standard procedures. Exemplary of such procedures are:

(1) PAF Radioreceptor Binding Assay (PAF Binding)

Platelet rich plasma is prepared by centrifugation of citrate-treated dog blood. Acidification to pH 6.5 with 0.15M citric acid and centrifugation for 10 minutes at $1000 \times g$ yields a platelet pellet which is then washed by resuspension in EDTA-Phosphate Buffered Saline (PBS) and recentrifuged. The washed platelet preparation is adjusted to $2 \times 10^7$ platelets/50 $\mu$l in 0.1% bovine serum albumin-PBS.

To a 400 $\mu$l microfuge tube containing 50 $\mu$l silicone oil (specific gravity 1.023) is added buffer, PAF standard or analog, or an extract to bring the aqueous volume to 150 $\mu$l. 50 $\mu$l of $^3$H-PAF (10,000 cpm, 45 Ci/mM) is added followed by $2 \times 10^7$ dog platelets. After mixing, incubating for 10 minutes at room temperature, and centrifuging for 1 minute in a Beckman Microfuge B ($8000 \times g$), the pellet is removed by clipping off the tip of the tube, the platelets are solubilized with 200 $\mu$l of 50% methanol and counted in 10 ml of Aquasol. A curve of 50-2500 pg/tube is obtained within 10 minutes of incubation which demonstrates high specificity and correlation with biological activity for PAF and its analogs. Results obtained with representative copounds of the present invention in this assay are summarized hereinafter in Tables I and II. $IC_{50}$ is drug concentration ($\mu$Molar) which inhibits PAF binding to dog platelets by 50%.

(2) Thromboxane Synthase Inhibition, In Vitro ($TXA_2$ Synth. Inhib.)

$TXA_2$ synthase activity is measured by following the conversion of $^{14}$C-prostaglandin endoperoxide ($PGH_2$) to $^{14}$C-thromboxane $A_2$ ($TXA_2$) using microsomal fractions from human platelets as enzyme source. In the aqueous incubation medium, the $TXA_2$ decomposes rapidly into $TXB_2$. The amount of $TXA_2$ synthase is adjusted so that under the conditions of the assay approximately 80-90% of the substrate, $PGH_2$, is converted to product in control tubes. To prepare $^{14}$C-$PGH_2$, $^{14}$C-AA (50-60 mCi/mmole; Rose Chem.) is incubated with sheep seminal vesicular gland microsomes for 1.5 minutes at 37° C. and then the $^{14}$C-$PGH_2$ is extracted with diethylether, purified on columns oof Sephadex LH-20 or silicic acid, and stored in acetone at $-70°$ C. Incubations are done as follows. Sufficient $^{14}$C-$PGH_2$ to yield a final substrate concentration of 10 $\mu$M (30,000 cpm) is added to the incubation tubes and then the acetone is removed under nitrogen. The tubes are placed in an ice bath and then 215 $\mu$l of ice cold phosphate buffered saline, 10 $\mu$l of ethanol (control) or of test drug in ethanol, and 25 $\mu$l of the microsomal suspension are added with mixing in that order as rapidly as possible. The tubes are incubated at 22° C. for 2 minutes, the reaction is stopped and then the radioactive products and the unconverted $PGH_2$ are extracted and analyzed by thin layer chromatography. The amount of $^{14}$C-$PGH_2$ converted to products is used as analyzed by thin layer chromatography. The amount of $^{14}$C-$PGH_2$ converted to products was used as a measure of $TXA_2$ synthase activity. Inhibitors were tested initially at a final concentration 100 $\mu$M. Results obtained with representative compounds of the present invention in this assay are summarized hereafter in Tables I and II. $IC_{50}$ is the drug concentration ($\mu$Molar) which inhibits $TXA_2$ activity by 50%.

(3) Inhibition of PAF Induced Guinea Pig Bronchoconstriction Test (Inhib. of PAF Broncho.)

Male guinea pigs (Hartley strain) weighing 300 to 500 g are anesthetized with urethane (2 g/kg) intraperitoneally and a polyethylene cannula is inserted into the jugular vein for drug administration. Tracheal pressure is recorded from a cannula inserted in the trachea and connected to a Statham pressure transducer. Propranolol (0.1 mg/kg) is administered intravenously five minutes before challenge with synthetic PAF, the animal's skeletal muscles are then paralyzed with succinylcholine (1.2 mg/kg i.v.), and the animal is respirated using a Harvard small animal respirator operating at 40 breaths/min and 2.5 cc stroke volume. Under these conditions PAF induces a dose-dependent increase in ventilatory pressure over a dose range of 0.5 to 5 $\mu$g/kg i.v. For screening purposes animals are challenged with a single dose of PAF (10 $\mu$g/kg i.v.).

Test compounds are screened by the intravenous route (10 mg/kg i.v., 1 min. pretreatment). The peak increase in ventilatory pressure (cm $H_2O$) is recorded for three control animals and five drug-treated animals and the percent inhibition determined from the following formula $$\frac{\text{Control} - \text{Drug Treated}}{\text{control}} \times 100$$

Results obtained with representative compounds of the invention in this test are summarized hereinafter in Tables I and II.

(4) Inhibition of PAF-Induced Rat Skin Wheal Test (Inhib. of PAF Skin Wheal)

This test evaluates the ability of compounds to inhibit PAF-induced increases in vascular permeability in the skin of Sprague-Dawley rats. PAF induces a dose-dependent skin wheal response in this system over a dose range of 0.0001 to 1 μg/0.05 ml injection. The profound vasoactive activity of PAF is emphasized by the fact that the maximum skin wheal response is considerably greater than that obtained with LTE and an $EC_{50}$ response is elicited at a 10-fold lower dose. 5 ng of PAF is injected intradermally into anesthetized rats which have been pretreated for 30 minutes with an antihistamine (pyrilamine maleate, 50 mg/kg, i.p.) and an antiserotonin compound (methylsergide maleate, 4 mg/kg, i.p.) Immediately thereafter, the compound is injected (5 mg/kg) intravenously into the tail vein of the animal. This is followed by an intravenous injection of Evan's blue dye (0.5% in saline). Thirty minutes later the animals are sacrificed and the increase in vascular permeability induced by the migration of dye into the injection point in the skin is determined. For this purpose, rats are sacrificed by cervical dislocation, the dorsal skin is removed, the long and short axis of each animal is measured with a metric vernier caliper and the average diameter is obtained. Results obtained are measured as % of migration of dye as compared to untreated animals. More specifically, results are measured as a percent inhibition of the diameters of the wheals formed in a treated animals as compared to untreated animals. Percent inhibition is $$\frac{\text{Control (Diameter)} - \text{Drug Treated (Diameter)}}{\text{Control (Diameter)}} \times 100$$

1-[2-Hydroxy-3-propyl-4-[4-[1-[3-(3-pyridinyl)propyl]-1H-tetrazol-5-yl]butoxy]phenyl]ethanone caused a 65±3% inhibition of PAF skin wheal in this test.

(5) Inhibition of PAF-Induced Platelet Aggregation (Inhib. of PAF Platelet Reduction)

Guinea pigs (anesthetized) are set up to withdraw blood for platelet counting. The animal is allowed to stabilize after completion of surgical procedures. The carotid catheter is allowed to bleed back blood and then is filled, prior to each sample withdrawal with sodium citrate 3.8% (0.15 ml). Blood (0.25 ml) is withdrawn 30 seconds prior to the PAF challenge and at 15, 30 and 60 seconds after the PAF challenge. This first PAF challenge is used as the control, assuming sufficient decreases in platelet count are observed. The amount of PAF used will be approximately 50 ng/kg, however, this can be increased to achieve the desired decreases in platelet count. Fifteen minutes after the control PAF challenge, intravenous drug dosing begins, with animals being dosed at 30 minute intervals; PAF challenge follows 15 minutes after each intravenous dose. Three intravenous drug doses are used in each experiment. Initial drug doses are 1, 3 and 10 mg/kg i.v. Inhibition of PAF platelet reduction at 3 mg/kg i.v. for representative compounds of the invention are summarized hereinafter in Tables I and II. Percent inhibition is $$\frac{\text{Control} - \text{Drug Treated}}{\text{Control}} \times 100.$$

(6) Leukotriene ($LTD_4$) Induced arrhythmia and Hypertension Test

Male Hartley guinea pigs are anesthetized with sodium pentobarbital and prepared for monitoring direct blood pressure and injecting drugs intravenously by catheterizing the right carotid artery and right jugular vein. Blood pressure, heart rate, and Lead II ECG are monitored in the conscious animal 24 hours later.

The oral activity of a drug is evaluated by pretreating animals 3 hours before the $LTD_4$ challenge. If a drug inhibits arrhythmias (as seen by abnormal beats), it is taken as being active.

Intravenous administration of $LTD_4$ 2.5 μg/kg) is associated with an increase in blood pressure lasting approximately 1–2 minutes followed by a decrease lasting approximately 5–15 minutes. Abnormal beats consisting of premature ventricular contractions, ST elevation or depression, atrioventricular conduction block, or dissociated p waves begin during the rise in blood pressure; the peak effect occurs approximately 40 seconds after $LTD_4$. The number of animals with abnormal beats within the first two minutes after the injection of $LTD_4$ over the total number of animals tested is presented in Table III. Inhibition of hypertension and hypotension are also presented in Table III. During the hypotensive response, the animal usually collapses during the 2nd or 3rd minute after $LTD_4$ and regains posture approximately 10 minutes after $LTD_4$.

TABLE I

| $R_1$ | $R_2$ | n | m | Het | PAF Binding $IC_{50}$ (μM) | $TXA_2$ Synth. Inhib. $IC_{50}$ (μM) | Inhib. of PAF Broncho % at 1 mg/kg i.v. (1 min. pretreat) | Inhib. of PAF Platelet Reduction % at 3 mg/kg i.v |
|---|---|---|---|---|---|---|---|---|
| H | H | 5 | 3 | 3-pyridyl | 0.15 | 0.1–1 | 96 ± 1 | 12 |
| H | H | 4 | 3 | 3-pyridyl | 0.125 | 0.1–1 | 99 ± 0 | — |
| H | H | 3 | 3 | 3-pyridyl | 0.25 | 0.01–0.1 | 53 ± 17 | — |

TABLE I-continued

| $R_1$ | $R_2$ | n | m | Het | PAF Binding $IC_{50}$ ($\mu$M) | $TXA_2$ Synth. Inhib. $IC_{50}$ ($\mu$M) | Inhib. of PAF Broncho % at 1 mg/kg i.v. (1 min. pretreat) | Inhib. of PAF Platelet Reduction % at 3 mg/kg i.v |
|---|---|---|---|---|---|---|---|---|
| H | H | 5 | 4 | 3-pyridyl | 0.275 | 0.1–1 | 58 ± 14 | 0 |
| H | H | 3 | 4 | 3-pyridyl | 0.45 | 0.1–1 | 59 ± 12 | 40 |
| H | H | 5 | 1 | 3-pyridyl | 0.8 | — | — | — |
| H | H | 4 | 2 | 3-pyridyl | 1.0 | — | −15 ± 6 | 48 |
| H | Ac | 5 | 3 | 3-pyridyl | 0.18 | 0.1–1 | 84.8 ± 11 | 31 |
| Cl | H | 5 | 4 | 3-pyridyl | 0.14 | 1.0 | — | 7 |
| H | H | 4 | 3 | 1-imidazolyl | 0.175 | 0.1–1 | 8 ± 8 | 3 |

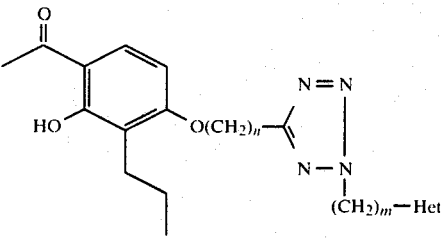

| n | m | Het | PAF Binding $IC_{50}$ ($\mu$M) | $TXA_2$ Synth. Inhib. $IC_{50}$ ($\mu$M) | Inhib. of PAF Broncho % at 1 mg/kg i.v. (1 min. pretreat) | Inhib. of PAF Platelet Reduction % at 3 mg/kg i.v |
|---|---|---|---|---|---|---|
| 5 | 3 | 3-pyridyl | >1 | 0.1–1 | 38 ± 11 | — |
| 4 | 3 | 3-pyridyl | >1 | — | 55 ± 9 | — |
| 3 | 3 | 3-pyridyl | >1 | — | 13 ± 7 | — |
| 5 | 4 | 3-pyridyl | 0.48 | 0.1–1 | 94 ± 6 | — |
| 3 | 4 | 3-pyridyl | 1 | — | 38 ± 14 | — |
| 5 | 1 | 3-pyridyl | >1 | — | — | — |
| 4 | 2 | 3-pyridyl | >1 | — | — | — |
| 4 | 3 | 1-imidazolyl | >1 | — | 30 ± 15 | — |

TABLE II

| | PAF Binding $IC_{50}$ ($\mu$M) | $TXA_2$ Synth. Inhib. $IC_{50}$ ($\mu$M) | Inhib. of PAF Broncho % at 1 mg/kg i.v. (1 min. pretreat) | Inhib. of PAF Platelet Reduction % at 3 mg/kg i.v |
|---|---|---|---|---|
| 1-[2-hydroxy-3-propyl-4-[[3-[1-[3-(3-pyridinyl)propyl]-1H—tetrazol-5-yl]phenyl]methoxy]phenyl]ethanone | 0.2 | 1.0 | — | — |
| 1-[5-chloro-2-hydroxy-3-propyl-4-[[3-[1-[3-(3-pyridinyl)propyl]-1H—tetrazol-5-yl]phenyl]methoxy]phenyl]ethanone | 0.025 | — | 43 ± 21 | 25 |

TABLE III

Inhibition of LTD$_4$ Induced Arrhythmias and Hypertension in Conscious Guinea Pigs (3 Hour Pretreatment)

| | n | m | Dose | ↑XABP (Δmm Hg) | No. Animals with Abnormal Beat/No. Tested | ↓XABP (Δmm Hg) |
|---|---|---|---|---|---|---|
| saline | — | — | — | 30 ± 4 | 12/12 | −45 ± 4 |
| control | 5 | 3 | 100 mg/kg po | 13 ± 8 | 0/4 | −20 ± 9 |
| | 3 | 3 | 100 mg/kg po | 14 ± 5 | 1/4 | −23 ± 10 |

The compounds of formula I, and salts thereof as herein described, can be administered orally or parenterally or in the form of an aerosol, for example, in the prophylactic treatment of bronchial asthma, with dosage adjustments for individual requirements. They can be administered therapeutically, for example, orally or parenterally or in the form of an aerosol, by incorporating a therapeutic dosage in a conventional dosage form, such as tablets, capsules, elixirs, suspensions, solutions, aerosols or the like. They can be administered in mixture with conventional pharmaceutical carriers or excipients, such as, for example, corn starch, calcium stearate, magnesium carbonate, calcium silicate, dicalcium phosphate, talc, lactose and the like. Moreover, they can be administered in the presence of buffers, or agents used to adjust to isotonicity, be subjected to conventional pharmaceutical expedients such as, for example, sterilization. As stated above, the dosage can be adjusted to individual requirements. They can also contain other therapeutically valuable substances.

The frequency with which any such dosage form will be administered to a mammal will vary, depending upon the quantity of active medicament present therein and the needs and requirements of the mammal. Dosages of a compound of formula I and its pharmaceutically acceptable salts contemplated for use in practicing the invention are in the range of from about 10 to about 1500 mg per day, either as a single dose or in divided doses. It is to be understood, however, that the above description and dosage strengths and the tablet and capsule and aerosol descriptions set forth herein are exemplary only and that they do not, to any extent, limit the scope or practice of this invention.

The examples which follow further illustrate the invention.

EXAMPLE 1

1-[2-Hydroxy-3-propyl-4-[5-(1H-tetrazol-5-yl)pentyloxy]phenyl ethanone

A mixture of 13.70 g 5-(4-acetyl-3-hydroxy-2-propylphenoxy)hexane-nitrile, 9.30 g sodium azide, 7.65 g ammonium chloride in 275 mL anhydrous dimethylformamide was stirred and heated at 120° for 90 hr. An additional 3.10 g of sodium azide and 2.57 g of ammonium chloride were added after 54 hr. The solvent was removed in vacuo and the residual solid was treated with 350 mL of water and acidified with 7 mL of 6N hydrochloric acid. The product was extracted with ethyl acetate and the dried (magnesium sulfate) extract was concentrated in vacuo to give an oil which was purified by high pressure liquid chromatography. Elution with toluene (70):ethyl acetate (25):acetic acid (10) gave a solid which was recrystallized from acetone-hexane. Filtration gave 8.55 g, mp 98°–100°, of 1-[2-hydroxy-3-propyl-4-[5-1H-tetrazol-5-yl)pentyloxy]phenyl ethanone. A second crop of 1.80 g, mp 94°–97°, was obtained.

Analysis. Calculated for $C_{17}H_{24}N_4O_3$: C, 61.43; H, 7.28; N, 16.85. Found: C, 61.54; H, 7.11; N, 16.85.

EXAMPLE 2

1-(2-Hydroxy-3-propyl-4-[5-[1-[3-(3-pyridinyl)propyl]-1H-tetrazol-5-yl]pentyloxy]phenyl]ethanone and
1-[2-Hydroxy-3-propyl-4-[5-[2-[3-(3-pyridinyl)propyl]-2H-tetrazol-5-yl]pentyloxy]phenyl]ethanone monohydrate sesquihydrochloride

Procedure A

A mixture of 7.35 g 1-[2-hydroxy-3-propyl-4-[5-(1H-tetrazol-5-yl)-pentyloxy]phenyl]ethanone, 6.22 g 3-(3-bromopropyl)pyridine hydrobromide, 9.20 g potassium carbonate, 75 mL anhydrous acetone and 75 mL anhydrous dimethylformamide was stirred and refluxed for 30 hr. The reaction mixture was filtered and the filtrate was concentrated in vacuo. The residual oil was dissolved in ethyl acetate and washed with saturated sodium bicarbonate solution and with saturated sodium chloride solution. The dried (magnesium sulfate) extract was concentrated in vacuo to an oil which was purified by high pressure liquid chromatography. Elution with triethyl amine (1.5):ethyl acetate (98.5) separated 1-[2-hydroxy-3-propyl-4-[5-[1-[3-(3-pyridinyl)propyl]-1H-tetrazol-5-yl]pentyloxy]phenyl]ethanone and 1-[-[2-hydroxy-3-propyl-4-[5-[2-[3-(3-pyridinyl)propyl]-2H-tetrazol-5-yl]pentyloxy]phenyl]ethanone.

The N-1 isomer, (1-[2-hydroxy-3-propyl-4-[5-[1-[3-(3-pyridinyl)propyl]-1H-tetrazol-5-yl]pentyloxy]phenyl]ethanone, was recrystallized from methylene chloride-ether to give 1.34 g, mp 97°–99°.

Analysis. Calculated for $C_{25}H_{33}N_5O_3$: C, 66.50; H, 7.37; N, 15.51. Found: C, 66.59; H, 7.31; N, 15.51.

The N-2 isomer, (1-[2-hydroxy-3-propyl-4-[5-[2-[3-(3-pyridinyl)propyl]-2H-tetrazol-5-yl]pentyloxy]phenyl]ethanone) was converted to the hydrochloride which was recyrstallized from ether to give 4.53 g, mp 80°–84°.

Analysis. Calculated for $C_{25}H_{33}N_5O_3 \cdot 1.0H_2O \cdot 1.5HCl$: C, 57.27; H, 7.02; N, 13.36; $Cl^-$, 10.14; $H_2O$, 3.44. Found: C, 57.07; H, 6.98; N, 13.36, $Cl^-$, 9.72; $H_2O$, 3.47.

EXAMPLE 3

1-[2-Hydroxy-3-propyl-4-[3-[1-[3-(3-pyridinyl)propyl]-1H-tetrazol-5-yl]propoxy]phenyl]ethanone and
1-[2-Hydroxy-3-propyl-4-[3-[2-[3-(3-pryidinyl)propyl]-2H-tetrazol-5-yl]propoxy]phenyl]ethanone

Procedure B

A mixture of 2.60 g 1-[2-hydroxy-3-propyl-4-[3-(1H-tetrazol-5-yl)propoxy]phenyl]ethanone, 2.40 g 3-(3-bromopropyl)pyridine hydrobromide, 3.60 mL triethylamine, 25 mL anhydrous acetone and 25 mL anhydrous dimethylformamide was stirred and refluxed for 5 hr. The reaction mixture was filtered and the filtrate was concentrated in vacuo. The residual oil was dissolved in ethyl acetate and washed with saturated sodium bicarbonate solution and with saturated sodium chloride solution. The dried magnesium sulfate extract was concentrated in vacuo to an oil which was purified by high pressure liquid chromatography. Elution with triethylamine (3):ethyl acetate (97) separated 1-[2-hydroxy-3-propyl-4-[3-[1-[3-(3-pyridinyl)propyl]-1H-tetrazol-5-yl]propoxy]phenyl]ethanone, which is the N-1 isomer, and 1-[2-hydroxy-3-propyl-4-[3-[2-[3-(3-pyridinyl)propyl]-2H-tetrazol-5-yl]propoxy]phenyl]ethanone, which is the N-2 isomer.

The N-1 isomer, was recrystallized from methylene chloride-ether to give 0.56 g, mp 101°–103°.

Analysis. Calculated for $C_{23}H_{29}N_5O_5$: C, 65.23; H, 6.90; N, 16.54. Found: C, 65.23; H, 6.99; N, 16.64.

The N-2 isomer, was isolated as an oil which solidified, mp 47°–49°.

Analysis. Calculated for $C_{23}H_{29}N_5O_3$: C, 65.23; H, 6.90; N, 16.54 Found: C, 65.03; H, 7.07; N, 16.56.

EXAMPLE 4

1-[2-Hydroxy-3-propyl-4-[4-[1-[3-(3-pyridinyl)propyl]-1H-tetrazol-5-yl]butoxy]phenyl]ethanone and
1-[2-Hydroxy-3-propyl-4-[4-[2-[3-(3-pyridinyl)propyl]-2H-tetrazol-5-yl]butoxy]phenyl]ethanone 1-2-Hydroxy-3-propyl-4-[4-(1H-tetrazol-5-yl)butoxy]phenyl]ethanone was allowed to react with 3-(3-bromopropyl)pyridine hydrobromide according to procedure B and the product was purified by high pressure liquid chromatography to give 1-[2-hydroxy-3-propyl-4-[4-[1-[3-(3-pyridinyl)propyl]-1H-tetrazol-5-yl]butoxy]phenyl]ethanone, which is the N-1 isomer, and 1-[2-hydroxy-3-propyl-4-[4-[2-[3-(3-pyridinyl)propyl]-2H-tetrazol-5-yl]butoxy]phenyl]ethanone, which is the N-2 isomer.

The N-1 isomer was obtained as a solid, mp 56°–59°.

Analysis. Calculated for $C_{24}H_{31}N_5O_3$: C, 65.88; H, 7.14; N, 16.01. Found: C, 65.60; H, 6.97; N, 15.98.

The N-2 isomer was isolated as an oil.

Analysis. Calculated for $C_{24}H_{31}N_5O_3$: C, 65.88, H, 7.14; N, 16.01. Found: C, 65.47; H, 6.90; N, 15.90.

EXAMPLE 5

1-[2-Hydroxy-3-propyl-4-[5-[1-[4-(3-pyridinyl)butyl]-1H-tetrazol-5-yl]pentyloxy]phenyl]ethanone and
1-[2-Hydroxy-3-propyl-4-[5-[2-[4-(3-pyridinyl)butyl]-2H-tetrazol-5-yl]pentyloxy]phenyl]ethanone 1-[2-Hydroxy-3-propyl-4-[5-(1H-tetrazol-5-yl)pentyloxy]phenyl]ethanone was allowed to react with 3-(4-bromobutyl)pyridine hydrobromide according to procedure B and the product was purified by high pressure liquid chromatography to give 1-[2-hydroxy-3-propyl-4-[5-[1-[4-(3-pyridinyl)butyl]-1H-tetrazol-5-yl]pentyloxy]phenyl]ethanone, which is the N-1 isomer, and 1-[2-hydroxy-3-propyl-4-[5-[2-[4-(3-pyridinyl)butyl]-2H-tetrazol-5-yl]pentyloxy]phenyl]ethanone, which is the N-2 isomer.

The N-1 isomer, mp 60°–62°, (from methylene chloride-ether) was obtained.

Analysis. Calculated for $C_{26}H_{35}N_5O_3$: C, 67.07; H, 7.58; N, 15.04. Found: C, 67.10; H, 7.72; N, 15.00.

The N-2 isomer was isolated as an oil.

Analysis. Calculated for $C_{26}H_{35}N_5O_3$: C, 67.07; H, 7.58; N, 15.04. Found: C, 67.11; H, 7.56; N, 15.10.

EXAMPLE 6

1-[2-Hydroxy-3-propyl-4-[3-[1-[4-(3-pyridinyl)butyl]-1H-tetrazol-5-yl]propoxy]phenyl]ethanone and
1-[2-Hydroxy-3-propyl-4-[3-[2-[4-(3-pyridinyl)butyl]-2H-tetrazol-5-yl]propoxy]phenyl]ethanone 1-[2-Hydroxy-3-propyl-4-[3-(1H-tetrazol-5-yl)propoxy]phenyl]ethanone was allowed to react with 3-(4-bromobutyl)pyridine hydrobromide according to procedure B and the product was purified by high pressure liquid chromatography to give 1-[2-hydroxy-3-propyl-4-[3-[1-[4-(3-pyridinyl)butyl]-1H-tetrazol-5-yl]propoxy]phenyl]ethanone, which is the N-1 isomer, and 1-[2-hydroxy-3-propyl-4-[3-[2-[4-(3-pyridinyl)butyl]-2H-tetrazol-5-yl]propoxy]phenyl]ethanone, which is the N-2 isomer.

The N-1 isomer, mp 58°–60°, (from methylene chloride-ether) was obtained.

Analysis. Calculated for $C_{24}H_{31}N_5O_3$: C, 65.88; H, 7.14; N, 16.01. Found: C, 66.12; H, 7.16; N, 16.24.

The N-2 isomer, was isolated as an oil.

Analysis. Calculated for $C_{24}H_{31}N_5O_3$: C, 65.88; H, 7.14; N, 16.01. Found: C, 65.52; H, 7.24; N, 15.77.

EXAMPLE 7

1-[2-Hydroxy-3-propyl-4-[5-[1-(3-pyridinyl)methyl-1H-tetrazol-5-yl]-pentyloxy]phenyl]ethanone and
1-[2-Hydroxy-3-propyl-4-[5-[2-(3-pyridinyl)methyl]-2H-tetrazol-5-yl]pentyloxy]phenyl]ethanone 1-[2-Hydroxy-3-propyl-4-[5-(1H-tetrazol-5-yl)pentyloxy]phenylethanone was allowed to reacted with 3-(chloromethyl)pyridine hydrochloride according to procedure A and the product was purified by high pressure liquid chromatography to give 1-[2-hydroxy-3-propyl-4-[5-[1-(3-pyridinyl)methyl-1H-tetrazol-5-yl]pentyloxy]phenyl]-ethanone, which is the N-1 isomer, and 1-[2-hydroxy-3-propyl-4-[5-[2-(3-pyridinyl)methyl]-2H-tetrazol-5-yl]pentyloxy]phenyl]ethanone, which is the N-2 isomer.

The N-1 isomer, mp 87°–89°, (from methylene chloride-ether) was obtained.

Analysis. Calculated for $C_{23}H_{29}N_5O_3$: C, 65.23; H, 6.90; N, 16.54. Found: C, 65.06; H, 7.01; N, 16.75.

The N-2 isomer, was obtained as a solid, mp 60°–63°.

Analysis. Calculated for $C_{23}H_{29}N_5O_3$: C, 65.23; H, 6.90; N, 16.54. Found: C, 65.23; H, 6.94; N, 16.61.

EXAMPLE 8

1-[2-Hydroxy-3-propyl-4-[4-[1-[2-(3-pyridinyl)ethyl]-1H-tetrazol-5-yl]butoxy]phenyl]ethanone and
1-[2-Hydroxy-3-propyl-4-[4-[2-[2-(3-pyridinyl)ethyl]-2H-tetrazol-5-yl]butoxy]phenyl]ethanone 1-[2-Hydroxy-3-propyl-4-[4-(1H-tetrazol-5-yl)butoxy]phenyl]ethanone was allowed to react with (3-(2-bromoethyl)pyridine hydrobromide according to procedure A and the product was purified by high pressure liquid chromatography to give 1-[2-hydroxy-3-propyl-4-[4-[1-[2-(3-pyridinyl)ethyl]-1H-tetrazol-5-yl]butoxy]phenyl]ethanone, which is the N-1 isomer, and 1-[2-hydroxy-3-propyl-4-[4-[2-[2-(3-pyridinyl)ethyl]-2H-tetrazol-5-yl]butoxy]phenyl]ethanone, which is the N-2 isomer.

The N-1 isomer, was obtained as a solid, mp 68°–71°.

Analysis. Calculated for $C_{23}H_{29}N_5O_3$: C, 65.23; H, 6.90; N, 16.54. Found: C, 64.90; H, 6.90; N, 16.20.

The N-2 isomer, was isolated as an oil.

Analysis. Calculated for $C_{23}H_{29}N_5O_3$: C, 65.23; H, 6.90; N, 16.54. Found: C, 64.97; H, 6.99; N, 16.24.

EXAMPLE 9

1-[2-Hydroxy-3-propyl-4-[5-[1-[4-(3-pyridinyl)butyl]-1H-tetrazol-5-yl]pentyloxy]phenyl]ethanone and
1-[5-Chloro-2-hydroxy-3-propyl-4-[5-[1-[4-(3-pyridinyl)butyl]-1H-tetrazol-5-yl]pentyloxy]phenyl]ethanone Phosphorus pentachloride (2.10 g) was added in portions to a stirred solution of 4.00 g 6-(4-acetyl-3-hydroxy-2-propylphenoxy)-N-[4-(3-pyridinyl)butyl]-hexanamide hydrochloride in 80 mL of anhydrous chloroform at 3°. The reaction mixture was stirred at 3° for an additional 0.25 hr and then at 25° for 1.75 hr. To this yellow solution stirred at 25° was added dropwise 12.3 mL of 1.5M hydrazoic acid in chloroform. The reaction mixture was stirred at 25° for 64 hr and then an additional 12.3 mL of 1.5M hydrazoic acid chloroform solution was added. After stirring for 24 hr at 25° and refluxing for 10 hr, the reaction mixture was washed with saturated sodium bicarbonate solution, dried (magnesium sulfate) and concentrated in vacuo to an oil which was purified by high pressure liquid chromatography. Elution with triethylamine (1:5):ethyl acetate (98.5) separated 1-[2-hydroxy-3-propyl-4-[5-[1-[4-(3-pyridinyl)butyl]-1H-tetrazol-5-yl]pentyloxy]phenyl]ethanone and 1-[5-chloro-2-hydroxy-3-propyl-4-[5-[1-[4-(3-pyridinyl)butyl]-1H-tetrazol-5-yl]pentyloxy]phenyl]ethanone.

1-[2-Hydroxy-3-propyl-4-[5-[1-[4-(3-pyridinyl)butyl]-1H-tetrazol-5-yl]pentyloxy]phenyl]ethanone (0.85 g, m.p. 61°–63°) was crystallized from methylene chloride-ether.

Analysis. Calculated for $C_{26}H_{35}N_5O_3$: C, 67.07; H, 7.58; N, 15.04. Found: C, 67.36; H, 7.58; N, 15.21.

1-[5-Chloro-2-hydroxy-3-propyl-4-[5-[1-[4-(3-pyridinyl)butyl]-1H-tetrazol-5-yl]pentyloxy]phenyl]ethanone was isolated as an oil, 0.330 g.

EXAMPLE 10

1-[2-Acetoxy-3-propyl-4-[5-[1-[3-(3-pyridinyl)propyl]-1H-tetrazol-5-yl]pentyloxy]phenyl]ethanone A solution of 100 mg of 1-[2-hydroxy-3-propyl-4-[5-[1-[3-(3-pyridinyl)propyl]-1-H-tetrazol-5-yl]pentyloxy]phenyl]ethanone in 2.0 mL of acetic anhydride and 2.0 mL of pyridine was stirred and heated at 80° for 18 hr. The solvent was removed in vacuo and the residual oil was purified by chromatography on silica gel. Elution with methylene chloride (90):95% methanol (10):concentrated ammonium hydroxide (0.05) gave a solid which was recrystallized from methylene chloride-ether to give 87 mg, mp 94°–96°, of 1-[2-acetoxy-3-propyl-4-[5-[1-[3-(3-pyridinyl)propyl]-1H-tetrazol-5-yl]pentyloxy]phenyl]ethanone.

Analysis. Calculated for $C_{27}H_{35}N_5O_4$: C, 65.70; H, 7.15; N, 14.19. Found: C, 65.33; H, 7.09; N, 13.92.

EXAMPLE 11

1-[2-Hydroxy-3-propyl-4-[4-[1-[3-(1H-imidazol-1-yl)propyl]-1H-tetrazol-5-yl]butoxy]phenyl]ethanone
and
1-[2-Hydroxy-3-propyl-4-[4-[2-[3-(1H-imidazol-1-yl)propyl]-2H-tetrazol-5-yl]butoxy]phenyl]-ethanone A mixture of 2.00 g 1-[2-hydroxy-3-propyl-4-[4-(1H-tetrazol-5-yl)butoxy]phenyl]ethanone, 1.69 g 3-bromopropyl-1H-imidazol-1-yl hydrobromide, 2.65 mL triethylamine, 20 mL anhydrous acetone and 20 mL anhydrous dimethylformamide was stirred and refluxed for 42 hr. The reaction mixture was filtered and the filtrate was concentrated in vacuo. The residual oil was dissolved in ethyl acetate and washed with sodium bicarbonate solution and with saturated sodium chloride solution. The dried (potassium carbonate) extract was concentrated in vacuo to an oil which was purified by high pressure liquid chromatography. Elution with triethyl amine (3):methanol (5):ethyl acetate (92) separated 1-[2-hydroxy-3-propyl-4-[4-[1-[3-(1H-imidazol-1-yl)propyl]-1H-tetrazol-5-yl]butoxy]phenyl]ethanone, which is the N-1 isomer, and 1-[2-hydroxy-3-propyl-4-[4-[2-[3-(1H-imidazol-1-yl)propyl]-2H-tetrazol-5-yl]butoxy]phenyl]ethanone, which is the N-2 isomer.

The N-1 isomer, was recrystallized from methylene chloride-ether to give 0.37 g, mp 72°–75°.

Analysis. Calculated for $C_{22}H_{30}N_6O_3$: C, 61.95; H, 7.09; N, 19.70. Found: C, 61.83; H, 7.21; N, 19.88.

The N-2 isomer, was isolated as an oil, 1.40 g.

Analysis. Calculated for $C_{22}H_{30}N_6O_3$: C, 61.95, H, 7.09; N, 19.70. Found: C, 61.65; H, 7.22; N, 19.69.

EXAMPLE 12

3-[4-Acetyl-3-hydroxy-2-propylphenoxy)methyl]benzonitrile

A mixture of 5.94 g 1-(2,4-dihydroxy-3-propylphenyl)ethanone, 6.00 g 3-cyanobenzyl bromide and 6.40 g potassium carbonate in 150 mL anhydrous acetone was stirred and refluxed for 4 hr. The reaction mixture was filtered and the filtrate was concentrated in vacuo to give a solid which was recrystallized from methylene chloride-ether to give 8.35 g, mp 115°–117°, 3-[4-acetyl-3-hydroxy-2-propylphenoxy)methyl]benzonitrile.

Analysis. Calculated for $C_{19}H_{19}NO_3$: C, 73.77; H, 6.19; N, 4.53. Found: C, 73.66; H, 6.22; N, 4.62.

EXAMPLE 13

1-[2-Hydroxy-3-propyl-4-[[3-(1H-tetrazol-5-yl)phenyl]methoxy]phenyl]ethanone

A mixture of 8.25 g 3-[(4-acetyl-3-hydroxy-2-propyl phenoxy)methyl]benzonitrile, 5.20 g sodium azide and 4.30 g ammonium chloride in 125 mL anhydrous dimethylformamide was stirred and heated at 120° for 6 hr. The solvent was removed in vacuo and the residue was treated with 250 mL water and acidified with 10 mL 6N hydrochloric acid. The resulting solid was recrystallized from ethanol-water to give 7.78 g, mp 194°–195° of 1-[2-hydroxy-3-propyl-4-[[3-(1H-tetrazol-5-yl)phenyl]methoxy]phenyl]ethanone.

Analysis. Calculated for $C_{19}H_{20}N_4O_3$: C, 64.76; H, 5.72; N, 15.90. Found: C, 64.60; H, 5.72; N, 16.17.

EXAMPLE 14

1-[2-Hydroxy-3-propyl-4-[[3-[1-[3-(3-pyridinyl)propyl]-1H-tetrazol-5-yl]phenyl]methoxy]phenyl]ethanone and
1-[2-Hydroxy-3-propyl-4-[[3-[2-[3-(3-pyridinyl)propyl]-2H-tetrazol-5-yl]phenyl]methoxy]-phenyl]ethanone A mixture of 1.00 g 1-[2-hydroxy-3-propyl-4-[[3-(1H-tetrazol-5-yl)phenyl]methoxy]phenyl]ethanone, 0.80 g 3-(3-bromopropyl)pyridine hydrobromide and 1.20 mL triethylamine (8.52 mmol in 10 mL anhydrous acetone and 10 mL anhydrous dimethylformamide was stirred and refluxed for 6 hr. The reaction mixture was filtered and the filtrate was concentrated in vacuo. The residual oil was dissolved in ethyl acetate and washed with saturated sodium bicarbonate solution and with saturated sodium chloride solution. The dried (magnesium sulfate) extract was concentrated in vacuo to an oil which was purified by high pressure liquid chromatography. Elution with triethyl amine (1.5):ethyl acetate (98.5) separated 1-[2-hydroxy-3-propyl-4-[[3-[1-[3-(3-pyridinyl)propyl]-1H-tetrazol-5-yl]phenyl]methoxy]-phenyl]ethanone, which is the N-1 isomer, and 1-[2-hydroxy-3-propyl-4-[[3-[2-[3-(3-pyridinyl)propyl]-2H-tetrazol-5-yl]phenyl]methoxy]phenyl]ethanone, which is the N-2 isomer.

The N-1 isomer, was recrystallized from ether to give 23 mg, mp 58°–61°.

The N-2 isomer, was recrystallized from ether-hexane to give 0.86 g, mp 82°–83°.

Analysis. Calculated for $C_{27}H_{29}N_5O_3$: C, 68.77; H, 6.20; N, 14.85. Found: C, 68.64; H, 6.45; N, 14.97.

EXAMPLE 15

1-[2-Hydroxy-3-propyl-4-[[3-[2-(1H-imidazol-1-yl)propyl]-2H-tetrazol-5-yl]phenyl]methoxy]phenyl]ethanone A mixture of 1.00 g 1-[2-hydroxy-3-propyl-4-[[3-(1H-tetrazol-1-yl)phenyl]methoxy]phenyl]ethanone, 0.77 g 3-bromopropyl-1H-imidazol-1-yl hydrobromide and 1.20 mL triethylamine in 10 mL anhydrous acetone and 10 mL anhydrous dimethylformamide was stirred and refluxed for 10 hr. The reaction mixture was filtered and the filtrate was concentrated in vacuo. The residual oil was dissolved in ethyl acetate and washed with saturated sodium bicarbonate solution and with saturated sodium chloride solution. The dried potassium carbonate extract was concentrated in vacuo to an oil which was purified by high pressure liquid chromatography. Elution with triethylamine (3):methanol (7.5):ethyl acetate (89.5) gave 0.77 g of 1-[2-hydroxy-3-propyl-4-[[3-[2-(1H-imidazol-1-yl)propyl]-2H-tetrazol-5-yl]phenyl]methoxy]phenyl]ethanone, mp 88°–91°.

Analysis. Calculated for $C_{25}H_{28}N_6O_3$: C, 65.20; H, 6.13; H, 18.25. Found: C, 64.99; H, 6.16; N, 18.10.

EXAMPLE 16

1-[5-Chloro-2-hydroxy-3-propyl-4-[[3-[1-[3-(3-pyridinyl)propyl]-1H-tetrazol-5-yl]phenyl]methoxy]phenyl]ethanone Phosphorus pentachloride (2.80 g) was added in portions to a stirred solution of 5.0 g 3-[(4-acetyl-3-hydroxy-2-propylphenoxy)methyl]-N-[3-(3-pyridinyl)propyl]benzamide in 100 mL of anhydrous chloroform at 3°. The reaction mixture was stirred at 3° for an additional 0.25 hr and 25° for 1.75 hr. To this yellow solution stirred at 25° was added dropwise 22 mL of 1.1M hydrazoic acid in chloroform. The reaction was stirred at 25° for 24 hr and then an additional 22.2 mL of 1.1M hydrazoic acid/chloroform solution was added. After stirring for 24 hr at 25° and refluxing for 10 hr, the reaction mixture was washed with saturated sodium bicarbonate solution, dried (magnesium sulfate) and concentrated in vacuo to an oil which was purified by high pressure liquid chromatography. Elution with triethylamine (1.5):ethyl acetate (98.5) gave 1-[5-chloro-2-hydroxy-3-propyl-4-[[3-[1-[3-(3-pyridinyl)propyl]-1H-tetrazol-5-yl]phenyl]methoxy]phenyl]ethanone.

1-[5-Chloro-2-hydroxy-3-propyl-4-[[3-[1-[3-(3-pyridinyl)propyl]-1H-tetrazol-5-yl]phenyl]methoxy]phenyl]ethanone was isolated as an oil, 0.875 g.

Analysis. Calculated for $C_{27}H_{28}ClN_5O_3$: C, 64.09; H, 5.58; Cl, 7.01; N, 13.84. Found: C, 63.73; H, 5.64; Cl, 6.92; N, 13.88.

EXAMPLE 17

1-[2-Hydroxy-3-propyl-4-[4-[1-[3-(3-pyridinyl)propyl]-1H-tetrazol-5-yl]butoxy]phenyl]ethanone and 1-[2-Hydroxy-3-propyl-4-[4-[2-[3-(3-pyridinyl)propyl]-2H-tetrazol-5-yl]butoxy]phenyl]ethanone

Procedure C

A mixture of 100 mg of 1-[2-hydroxy-3-propyl-4-[4-(1H-tetrazol-5-yl)-butoxy]phenyl]ethanone, 94 mg of 3-(3-bromopropyl)pyridine and 0.08 mL of tri-n-butyl-stannyl oxide dissolved in 2.0 mL anhydrous toluene was stirred at 25° for 2 hr and then heated at 80° for 16 hr. The reaction mixture was treated with one drop of acetic acid and stirred 1 hr and then was concentrated in vacuo to an oil which was purified by preparative thin layer chromatography on silica gel plates. Elution with triethyl amine (3):ethyl acetate (97) separated 1-[2-hydroxy-3-propyl-4-[4-[1-[3-(3-pyridinyl)propyl]-1H-tetrazol-5-yl]butoxy]phenyl]ethanone, which is the N-1 isomer, and 1-[2-hydroxy-3-propyl-4-[4-[2-[3-(3-pyridinyl)propyl]-2H-tetrazol-5-yl]butoxy]phenyl]ethanone, which is the N-2 isomer.

The N-1 isomer was oscillated as an oil, 55 mg.

The N-2 isomer was isolated as a solid 29 mg, mp 57°–61°.

The NMR spectra of the above N-1 and N-2 isomers obtained by this procedure were identical to the spectra obtained for these compounds prepared by Procedure B.

EXAMPLE 18

7-(4-Acetyl-3-hydroxy-2-propylphenoxy)heptanoic acid

A mixture of 5.8 g of 1-(2,4-dihydroxy-3-propylphenyl)ethanone, 5.4 ml of 7-bromoheptanenitrile and 8.3 g of anhydrous potassium carbonate in 50 ml of dimethyl formamide was stirred and heated at 75° for 20 hours. The reaction mixture was filtered and the filtrate was concentrated on the oil pump. The residual oil was chromatographed on 200 g of silica gel using 5% ethyl acetate-toluene to give 7.5 g (83% yield) of 7-(4-acetyl-3-hydroxy-2-propylphenoxy)heptane nitrile. This was dissolved in 200 ml of ether-methanol (1:1) and cooled in an ice bath while a stream of hydrochloric acid gas was introduced for 10 minutes. The reaction mixture was kept at 3° for 1 hour and at room temperature for 16 hours. Water (40 ml) was added and most of the solvent was removed in vacuo. The residue was treated with sodium bicarbonate solution to basify and the product was extracted with ether. The crude product was dissolved in 140 ml of methanol, treated with 120 ml of 1N sodium hydroxide and the solution was heated on the steam bath for 10 minutes and left at room temperature for 66 hours. The methanol was removed in vacuo and the aqueous solution was extracted with ether. The basic aqueous layer was acidified and extracted with ether. The dried (over magnesium sulfate) extract was concentrated and chromatographed on 50 g of silica gel. Elution with acetic acid (5): ethyl acetate (25): toluene (70) and crystallization of the combined pure fractions from ether-hexane gave 2.20 g, mp 64°–66°, of 7-(4-acetyl-3-hydroxy-2-propylphenoxy)heptanoic acid.

Analysis Calculated for $C_{18}H_{26}O_5$: C, 67.06; H, 8.13. Found: C, 67.08; H, 7.97.

EXAMPLE 19

5-(4-Acetyl-3-hydroxy-2-propylphenoxy)pentanoic acid methyl ester

A mixture of 2.92 g of 1-(2,4-dihydroxy-3-propylphenyl)ethanone, 2.91 g of methyl 5-bromopentanoate and 3.1 g of anhydrous potassium carbonate in 35 ml of anhydrous dimethyl formamide was stirred and heated at 75° for 16 hours. The usual workup followed by chromatography on 350 g of silica gel and elution with 5% ethyl acetate-toluene gave 3.07 g (66% yield) of 5-(4-Acetyl-3-hydroxy-2-propylphenoxy) pentanoic acid methyl ester, the titled compound, as an oil.

Analysis Calculated for $C_{17}H_{24}O_5$: C, 66.21; H, 7.85. Found: C, 66.39; H, 7.80.

EXAMPLE 20

5-(4-Acetyl-3-hydroxy-2-propylphenoxy)pentanoic acid

A solution of 2.97 g of 5-(4-acetyl-3-hydroxy-2-propylphenoxy)pentanoic acid methyl ester in 50 ml of methanol and 50 ml of 1.0N sodium hydroxide was heated at reflux for 10 minutes. The usual workup followed by recrystallization from ether-hexane gave 2.69 g (95% yield), mp 97°–102°, of 5-(4-acetyl-3-hydroxy-2-propylphenoxy)pentanoic acid, the titled compound.

Analysis Calculated for $C_{16}H_{22}O_5$: C, 65.29; H, 7.53. Found: C, 65.46; H, 7.77.

EXAMPLE 21

1-[2-Hydroxy-4-(3-hydroxypropoxy)-3-propylphenyl]ethanone

A mixture of 5.80 g of 1-(2,4-dihydroxy-3-propylphenyl)ethanone, 3.6 ml of 3-bromo-1-propanol and 8.3 g of anhydrous potassium carbonate in 50 ml of anhydrous dimethyl formamide was stirred at 75° for 64 hours. The reaction mixture was concentrated in vacuo, the residue was acidifed and extracted with ethyl acetate. The extract was dried over magnesium sulfate and concentrated in vacuo to 8.7 g of an oil which was chromatographed on 150 g of silica gel. Elution with 40% ethyl acetate-toluene gave 2.84 g which was crystallized from ether-hexane to yield 2.14 g, mp 57°–59°, (28% yield) of 1-[2-hydroxy-4-(3-hydroxypropoxy)-3-propylphenyl]ethanone, the titled compound.

Analysis Calculated for $C_{14}H_{20}O_4$: C, 66.65; H, 7.99. Found: C, 66.56; H, 7.99.

Additional fractions (1.42 g) of slightly impure product were obtained.

EXAMPLE 22

3-(4-Acetyl-3-hydroxy-2-propylphenoxy)propanoic acid

A solution of 2.00 g of 1-[2-hydroxy-4-(3-hydroxypropoxy)-3-propylphenyl]ethanone in 30 ml of acetone was added dropwise over 45 minutes to a stirred, ice cooled solution of 4.0 ml of Jones reagent in 10 ml of acetone. After 15 additional minutes, the cooling bath was removed and the reaction mixture was stirred at 23° for 15 minutes. Jones reagent (0.5 ml) was added and stirring was continued for 15 minutes. The reaction mixture was concentrated in vacuo and the residue was treated with water and extracted with ether. The ether extract was washed with three portions of 1N sodium hydroxide and the aqueous layers were combined and acidified. The product was extracted with ether and the dried (over magnesium sulfate) extract was concentrated in vacuo to a solid (1.48 g). Recrystallization from ether-hexane gave 1.21 g, mp 142°–146°, (57% yield) of 3-(4-acetyl-3-hydroxy-2-propylphenoxy)propanoic acid, the titled compound.

Analysis Calculated for $C_{14}H_{18}O_5$: C, 63.15; H, 6.81. Found: C, 62.95; H, 7.01.

EXAMPLE 23

5-(4-Acetyl-3-hydroxy-2-propylphenoxy)-N-[4-(3-pyridinyl)butyl]pentanamide

To a solution of 0.686 g 5-(4-acetyl-3-hydroxy-2-propylphenoxy)pentanoic acid in 10 mL anhydrous dimethyl formamide stirred at 5° was added 0.55 mL of diphenylphosphoryl azide dropwise followed by 0.70 mL of triethylamine added dropwise. The reaction mixture was stirred at 5° for 1.5 hour and then 0.385 g of 3-pyridine butanamine was added dropwise. The reaction mixture was stirred at 5° for 3 hours and then at 25° for 16 hours. The solvent was removed in vacuo and the residual oil was dissolved in ethyl acetate and the solution was washed with saturated sodium bicarbonate solution and with saturated sodium chloride solution. The dried (magnesium sulfate) extract was concentrated in vacuo to an oil which was chromatographed on 40 g silica gel. Elution with methylene chloride (90): 95% $CH_3OH$ (10): concentrated ammonium hydroxide (0.05) gave a yellow oil which was crystallized from acetone-hexane. Filtration gave 0.665 g, mp 76°–78°, (67% yield) of the title compound.

Analysis Calculated for $C_{25}H_{34}N_2O_4$: C, 70.40; H, 8.02; N, 6.57. Found: C, 70.50; H, 8.00; N, 6.55.

EXAMPLE 24

3-(4-Acetyl-3-hydroxy-2-propylphenoxy)-N-[4-(3-pyridinyl)butyl]propanamide

To a solution of 0.700 g of 3-(4-acetyl-3-hydroxy-2-propylphenoxy)propanoic acid and 0.469 g of 1,1'-carbonyldiimidazole in 25 mL of anhydrous tetrahydrofuran at 25° was added 0.434 g of 3-pyridine butanamine. The reaction mixture was stirred for 2 hours and then the solvent was removed in vacuo. The residual oil was dissolved in ethyl acetate and the solution was washed with sodium bicarbonate solution and with saturated sodium chloride solution. The product was chromatographed on 40 g of silica gel. Elution with methylene chloride (90): 95% methanol (10): concentrated ammonium hydroxide (0.05) gave the pure product which was recrystallized from methylene chloride-ether to give the title compound, mp 110°–112°, in 63% yield.

Analysis Calculated for $C_{23}H_{30}N_2O_4$: C, 69.32; H, 7.59; N, 7.03. Found: C, 69.08; H, 7.57; N, 7.07.

EXAMPLE 25

| | TABLET FORMULATION (Wet Granulation) | | |
|---|---|---|---|
| | | mg/tablet | |
| Item | Ingredient | 100 mg | 500 mg |
| 1. | 1-[2-Hydroxy-3-propyl-4-[4-[1-[3-(3-pyridinyl)propyl]-1H—tetrazol-5-yl]butoxy]phenyl]ethanone | 100 | 500 |
| 2. | Lactose | 30 | 150 |
| 3. | Pregelatinized Starch | 6 | 30 |
| 4. | Microcrystalline Cellulose | 30 | 150 |
| 5. | Magnesium Stearate | 1 | 6 |
| | | 167 mg | 836 mg |

(1) Mix Items 1, 2, 3, and 4 and granulate with water.
(2) Dry the granulation at 50° C.
(3) Pass the granulation through suitable milling equipment.
(4) Add Item 5 and mix for three minutes; compress on a suitable press.

EXAMPLE 26

| | CAPSULE FORMULATION | | |
|---|---|---|---|
| | | mg/capsule | |
| Item | Ingredient | 100 mg | 500 mg |
| 1. | 1-[2-Hydroxy-3-propyl-4-[4-[1-[3-(3-pyridinyl)propyl]-1H—tetrazol-5-yl]butoxy]phenyl]ethanone | 100 | 500 |
| 2. | Corn Starch (Pregelatinized) | 8 | 40 |
| 3. | Modified Starch | 4 | 20 |
| 4. | Talc | 4 | 20 |
| 5. | Magnesium Stearate | 1 | 2 |
| | | 117 mg | 582 mg |

(1) Mix Items 1, 2 and 3 and wet granulate with water. Dry at 45° C. overnight.
(2) Mill through suitable screen using appropriate milling equipment.
(3) Add Items 4 and 5 and mix for five minutes.
(4) Fill into suitable capsule.

EXAMPLE 27

| | INHALATION AEROSOL FORMULATION (SOLUTION) | |
|---|---|---|
| Item | | % w/w |
| 1. | 1-[2-Hydroxy-3-propyl-4-[4-[1-[3-(3-pyridinyl)propyl]-1H—tetrazol-5-yl]butoxy]phenyl]ethanone | 1 |
| 2. | Ethyl Alcohol | 30 |
| 3. | Ascorbic Acid | 0.5 |
| 4. | Propellant 12 | 54.8 |
| 5. | Propellant 114 | 13.7 |
| | Total | 100% |

(1) Dissolve items 1 and 3 in 2.
(2) Fill solution from step #1 into a suitable glass bottle, insert valve and crimp to seal container.
(3) Pressure fill a 80:20 mixture of items 4 and 5 into the container.
Note:
A suitable valve may be used to deliver 25 to 100 microliters in volume. Propellant 12 is dichlorodifluoromethane. Propellant 114 is dichlorotetrafluoroethane.

We claim:

1. A compound of the formula

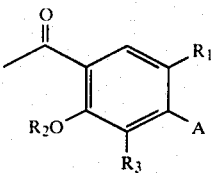

wherein $R_1$ is hydrogen or halogen; $R_2$ is hydrogen or $C_2$-$C_4$ alkanoyl; $R_3$ is hydrogen or $C_1$-$C_6$ alkyl; A is
—O—$(CH_2)_n$—B .

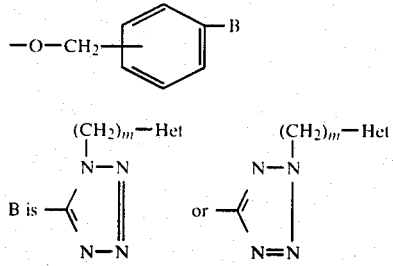

Het is 3-pyridyl or 4-pyridyl; n is an integer from 3 to 8; and m is an integer from 1 to 6; or a pharmaceutically acceptable acid addition salt thereof.

2. A compound in accordance with claim 1, wherein $R_1$ is hydrogen, $R_2$ is hydrogen, $R_3$ is propyl, A is —O—$(CH_2)_n$—B, and B is

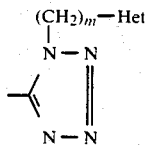

Het is 3-pyridyl, n is an integer from 3 to 5, and m is an integer from 1 to 4.

3. A compound in accordance with claim 2, wherein $R_1$ is hydrogen, $R_2$ is hydrogen, $R_3$ is propyl, A is —O—$(CH_2)_n$—B, B is

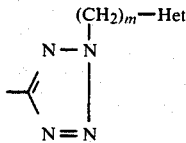

Het is 3-pyridyl, n is an integer from 3 to 5, and m is an integer from 1 to 4.

4. A compound in accordance with claim 2, wherein m is an integer from 3 to 4.

5. A compound in accordance with claim 3, wherein m is an integer from 3 to 4.

6. A compound in accordance with claim 4, 1-[2-hydroxy-3-propyl-4-[5-[1-[3-(3-pyridinyl)propyl]-1H-tetrazol-5-yl]pentyloxy]phenyl]ethanone or a pharmaceutically acceptable acid addition salt thereof.

7. A compound in accordance with claim 4, 1-[2-hydroxy-3-propyl-4-([3-[1-[3-(3-pyridinyl)propyl]-1H-tetrazol-5-yl]propoxy]phenyl]ethanone or a pharmaceutically acceptable acid addition salt thereof.

8. A compound in accordance with claim 4, 1-[2-hydroxy-3-propyl-4-[5-[1-[4-(3-pyridinyl)butyl]-1H-tetrazol-5-yl]pentyloxy]phenyl]ethanone or a pharmaceutically acceptable acid addition salt thereof.

9. A compound in accordance with claim 4, 1-[2-hydroxy-3-propyl-4-[3-[1-[4-(3-pyridinyl)butyl]-1H-tetrazol-5-yl]propoxy]phenyl]ethanone or a pharmaceutically acceptable acid addition salt thereof.

10. A compound in accordance with claim 4, 1-[2-hydroxy-3-propyl-4-[4-[1-[3-(3-pyridinyl)propyl]-1H-tetrazol-5-yl]butoxy]phenyl]ethanone, or a pharmaceutically acceptable acid addition salt thereof.

11. A compound in accordance with claim 5, 1-[2-hydroxy-3-propyl-4-[5-[2-[4-(3-pyridinyl)butyl]-2H-tetrazol-5-yl]pentyloxy]phenyl]ethanone or a pharmaceutically acceptable addition salt thereof.

12. A compound in accordance with claim 3, 1-[2-hydroxy-3-propyl-4-[[3-[1-(3-pyridinyl)propyl]-1H-tetrazol-5-yl]phenyl]methoxy]phenyl]ethanone, or a pharmaceutically acceptable acid addition salt thereof.

13. A compound in accordance with claim 3, 1-[2-hydroxy-3-propyl-4-[[3-[2-[3-(3-pyridinyl)propyl]-2H-tetrazol-5-yl]phenyl]methoxy]phenyl]ethanone, or a pharmaceutically acceptable acid addition salt thereof.

14. A compound in accordance with claim 3, wherein $R_1$ is chlorine, $R_2$ is hydrogen, $R_3$ is propyl; and B is

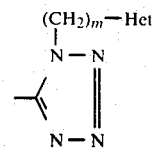

Het is 3-pyridyl, n is an integer from 3 to 5, and m is an integer from 1 to 4.

15. A compound in accordance with claim 14, 1-[5-chloro-2-hydroxy-3-propyl-4-[[3-[1-[3-(3-pyridinyl)propyl]-1H-tetrazol-5-yl]phenyl]methoxy]phenyl]ethanone, or a pharmaceutically acceptable acid addition salt thereof.

16. A compound in accordance with claim 14, 1-[5-chloro-2-hydroxy-3-propyl-4-[5-[1-[4-(3-pyridinyl)butyl]-1H-tetrazol-5-yl]pentyloxy]phenyl]ethanone, or a pharmaceutically acceptable acid addition salt thereof.

17. A compound in accordance with claim 3, 1-[2-acetoxy-3-propyl-4-[5-[1-[3-(3-pyridinyl)propyl]-1H-tetrazol-5-yl]pentyloxy]phenyl]ethanone, or a pharmaceutically acceptable acid addition salt thereof.

18. A pharmaceutical composition comprising an antiallergically effective amount of a compound of the formula

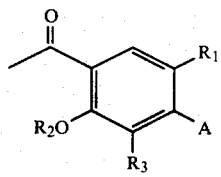

wherein $R_1$ is hydrogen or halogen, $R_2$ is hydrogen or $C_2$-$C_4$ alkanoyl; $R_3$ is $C_1$-$C_6$ alkyl; A is —O—$(CH_2)_n$—B or Het is 3-pyridyl or 4-pyridyl; n is an integer from 3 to 8; and m is an integer from 1 to 6; or a pharmaceutically acceptable acid addition salt thereof, and a pharmaceutical carrier.

19. A pharmaceutical composition in accordance with claim 18, wherein $R_1$ is hydrogen, $R_2$ is hydrogen, $R_3$ is propyl, A is —O—$(CH_2)_n$—B; and B is

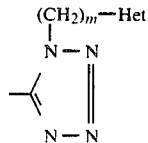

Het is 3-pyridyl, n is an integer from 3 to 5; and m is an integer from 1 to 4.

20. A pharmaceutical composition in accordance with claim 19, wherein the compound of formula I is 1-[2-hydroxy-3-propyl-4-[5-[1-[3-(3-pyridinyl)propyl]-1H-tetrazol-5-yl]pentyloxy]phenyl]ethanone, or a pharmaceutically acceptable acid addition salt thereof.

21. A method for treatment of allergy which comprises administering to a mammal in need thereof an effective amount of a compound of the formula

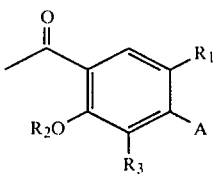

wherein $R_1$ is hydrogen or halogen, $R_2$ is hydrogen or $C_2$-$C_4$ alkanoyl; $R_3$ is $C_1$-$C_6$ alkyl, A is —O—$(CH_2)_n$B; or
Het is 3-pyridyl or 4-pyridyl; n is an integer from 3 to 8; and m is an integer from 1 to 6; or a pharmaceutically acceptable acid addition salt thereof.

22. A method in accordance with claim 21, wherein $R_1$ is hydrogen, $R_2$ is hydrogen, $R_3$ is propyl, A is —O—$(CH_2)_n$—B; B is

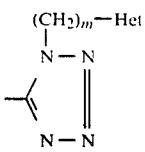

Het is 3-pyridyl, n is an integer from 3 to 5; and m is an integer from 1 to 4.

23. A method in accordance with claim 22, wherein the compound of formula I is 1-[2-hydroxy-3-propyl-4-[5-[1-[3-(3-pyridinyl)propyl]-1H-tetrazol-5-yl]pentyloxy]phenyl]ethanone, or a pharmaceutically acceptable acid addition salt thereof.

* * * * *

UNITED STATES PATENT AND TRADEMARK OFFICE
CERTIFICATE OF CORRECTION

PATENT NO. : 4,663,332
DATED : May 5, 1987
INVENTOR(S) : Matthew Carson and Ronald A. LeMahieu It is certified that error appears in the above—identified patent and that said Letters Patent is hereby corrected as shown below:

In claim 3, line 1, delete "claim 2" and insert therefor --claim 1 --.

In claim 12, line 1, delete "claim 3" and insert therefor --claim 2--.

In claim 14, line 1, delete "claim 3" and insert therefor --claim 2--.

In claim 17, line 1, delete "claim 3" and insert therefor --claim2--.

In claim 18, line 7, and also in claim 21, line 7, insert

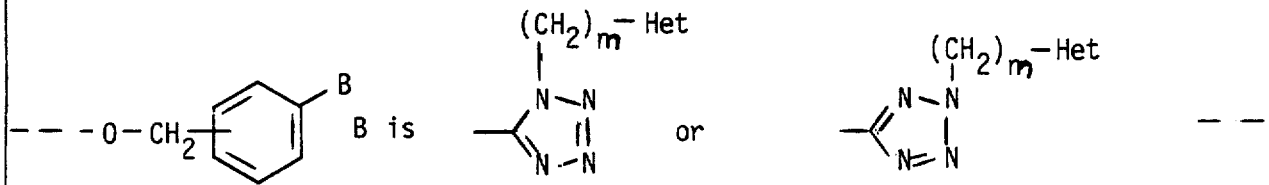

Signed and Sealed this

Twentieth Day of October, 1987

Attest:

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,663,332
DATED : May 5, 1987
INVENTOR(S) : Matthew Carson and Ronald A. LeMahieu It is certified that error appears in the above-identified patent and that said Letters Patent is hereby corrected as shown below:

In claim 7, column 29, line 64, delete "hydroxy-3-propyl-4-([3-[1-[3-(3-pyridinyl)-propyl-1H-" and insert therefor -- hydroxy-3-propyl-4-[3-[1-[3-(3-pyridinyl)-propyl]-1H- --.

In claim 12, column 30, line 16, delete "hydroxy-3-propyl-4-[[3-[1-(3-pyridinyl)propyl]-1H-tet-" and insert therefor -- hydroxy-3-propyl-4-[[3-[1-[3-(3-pyridinyl)propyl]-1H-tet- --.

Signed and Sealed this

Seventh Day of June, 1988

Attest:

DONALD J. QUIGG

Attesting Officer      Commissioner of Patents and Trademarks